United States Patent [19]

Yamamoto

[11] Patent Number: 5,047,526

[45] Date of Patent: Sep. 10, 1991

[54] DEHYDROGENATIVE SILYLATION PROCESS OF ORGANIC COMPOUNDS HAVING ACTIVE HYDROGEN

[75] Inventor: Keiji Yamamoto, Yokohama, Japan

[73] Assignee: Shin-Etsu Chemical Co., Ltd., Japan

[21] Appl. No.: 369,964

[22] Filed: Jun. 22, 1989

[30] Foreign Application Priority Data

Jun. 29, 1988 [JP] Japan .................................. 63-162173

[51] Int. Cl.$^5$ .......................... C07F 7/08; C07F 7/18; C07F 7/10; C07D 205/00
[52] U.S. Cl. .................................... 540/200; 556/410; 556/413; 556/442; 556/470; 544/69
[58] Field of Search ............... 556/413, 442, 470, 410; 540/200; 544/69

[56] References Cited

PUBLICATIONS

Noll, "Chemistry and Technology of Silicones", Academic Press, N.Y. (1968), p. 92.
"A Stereocontrolled Synthesis of (+)-Thienamycin", by Salzmann et al.; J. Am. Chem. Soc. 1980, 102, 6161-6163.
"Protection of Hydroxyl Groups as tert-Butyldimethylsilyl Derivatives", by Corey et al.; Journal of the American Chemical Society; Aug. 23, 1972; pp. 6190 & 6191.

*Primary Examiner*—Paul F. Shaver
*Attorney, Agent, or Firm*—Lowe, Price, LeBlanc & Becker

[57] ABSTRACT

A dehydrogenative silylation process of organic compounds having active hydrogen which comprises reacting an organic compound having active hydrogen with t-butyldimethylsilane in the presence of a catalyst which is a metal of Group VIII of the periodic table or its compound. The reaction may be carried out in a solvent. When the organic compound is a strongly acidic compound, the reaction may be carried out without use of any catalyst.

18 Claims, No Drawings

DEHYDROGENATIVE SILYLATION PROCESS OF ORGANIC COMPOUNDS HAVING ACTIVE HYDROGEN

BACKGROUND OF THE INVENTION

1. Field of the Invention

This invention relates to a novel dehydrogenative silylation process wherein a tert-butyldimethylsilyl is introduced into organic compounds.

2. Description of the Prior Art

In recent trends for the preparation of β-lactam antibiotics or prostaglandins, an —NH group and/or —OH group are usually protected with a t-butyldimethylsilyl group. This is because the protective group is resistant to the Grignard reaction, the Wittig reaction, diisobutyl aluminum hydride reduction and the Jones oxidation but can be very readily eliminated by the attack of F ions (see T. N. Saltzman et al., J. Am. Chem. Soc. 102, 6161 (1980)).

Silylating agents conventionally used to protect active hydrogen with a t-butyldimethylsilyl group are a chlorosilane of the formula, $(CH_3)_3CSi(CH_3)_2$-Cl, without exception. The reason why this chlorosilane is utilized for this purpose is believed due to the fact that studies in this field have been made mainly by the Corey procedure (E. J. Corey et al, J. Am. Chem. Soc., 94, 6190 (1972)).

The use of the tert-butyldimethylchlorosilane has the following drawbacks: solid quaternary ammonium salts secondarily produced during the silylation reaction have to be removed; since the chlorosilane causes reactor materials, particularly iron, to be corroded, a glass-lined reactor must be used; and the t-butyldimethylchlorosilane is solid at room temperature and is rather difficult to handle.

SUMMARY OF THE INVENTION

It is accordingly an object of the invention to provide a novel dehydrogenative silylation process which overcomes the drawbacks of the prior art processes by the use of t-butyldimethylsilane which is liquid at normal temperatures, is corrosion-free and is easy in handling.

It is another object of the invention to provide a novel dehydrogenative silylation process whereby side products except for hydrogen are not formed and any specific removal procedure is not necessary as in the prior art processes.

It is a further object of the invention to provide a silylation process for protecting organic compounds having active hydrogen in a high efficiency.

The above objects can be achieved, according to the invention, by a dehydrogenative silylation process which comprises reacting tert-butyldimethylsilane of the formula, $(CH_3)_3CSiH(CH_3)_2$, and an organic compound having active hydrogen reactive with the t-butyldimethylsilane at a temperature of from 20° C. to 200° C. The above reaction should preferably be carried out in the presence of a catalyst for the silylation.

DETAILED DESCRIPTION AND EMBODIMENTS OF THE INVENTION

In the silylation process of the invention, it is essential to use tert-butyldimethylsilane. The t-butyldimethylsilane is a compound which has a boiling point of 82° C. and is liquid at normal temperatures. This compound is prepared in large amounts without use of expensive tert-butyl lithium according to the following reaction sequence

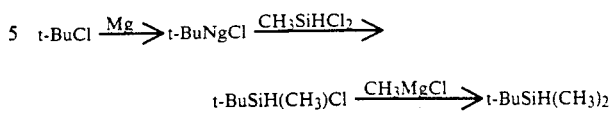

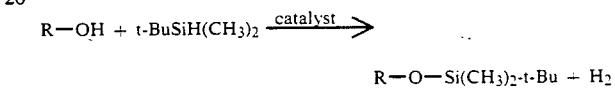

In the above formula, t-Bu represents a tertiary-butyl group.

The organic compounds which are reacted with the t-butyldimethylsilane should have active hydrogen in the molecule. Such active hydrogen means a hydroxyl group, an amino group, a carboxyl group or the like. These groups may be silylated according to the process of the invention in the following manner.

(1) Silylation of alcohols

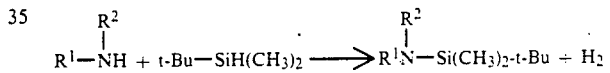

wherein R represents a linear or branched alkyl group having from 1 to 10 carbon atoms, an aryl group such as phenyl, tolyl, xylyl or the like, an aralkyl group such as benzyl, phenylethyl, methylphenyl or the like. These groups may be unsubstituted or substituted with a halogen atom, an ether group or the like. The halogen atom includes, chlorine bromine, iodine or fluorine.

(2) Silylation of primary and secondary amines

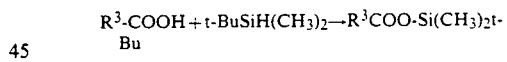

wherein $R^1$ and $R^2$ have, respectively, the same meaning as defined with respect to R provided that $R^2$ is hydrogen when primary amines are used for silylation.

(3) Silylation of organic acids $R^3$-COOH + t-BuSiH$(CH_3)_2$ → $R^3$COO-Si$(CH_3)_2$t-Bu wherein $R^3$ has the same meaning as defined with respect to R.

Specific examples of the organic compounds which are particularly suitable and useful for industrial purposes include alcohols such as 3-phenyl-1-propanol, benzyl alcohol, α-methylbenzyl alcohol, cyclohexanol and the like; amines such as morpholine, benzylamine, α-methylbenzylamine, 4-hydroxymethyl-2-azetidinone and the like; and organic acids such as 3-phenylpropionic acid, 2-methylbutanoic acid and the like. Of these, 4-hydroxymethyl-2-azetidinone is preferred although the above-specified compounds are all useful.

The reaction between t-butyldimethylsilane and organic compounds having active hydrogen proceeds at a temperature of from 20° C. to 200° C., preferably from 40° to 150° C.

This reaction should preferably be carried out in the presence of a catalyst which is a metal of Group VIII of the periodic table or a compound of the metal. Examples of the catalyst include Ru, Rh, Pd, Ru-carbon, Rh-carbon, Pd-carbon, PdCl$_2$, [Pd($\pi^3$-C$_3$H$_5$)Cl]$_2$,

and the like. Of these, Pd(II) complexes are preferred. This is because these complexes are reduced with t-butyldimethylsilane during the reaction to precipitate metallic Pd, which has very high catalytic activity for the silylation. In addition, Pt and platinum compounds such as $H_2PtCl_6$ may also be used, but they are not favorable when compounds to be silylated have unsaturated bonds such as double or triple bonds in the molecule. This is because such unsaturated bonds react with t-butyldimethylsilane thereby causing hydrosilation. The amount of the catalyst is generally in the range of from 0.12 mole % to 20 mole %, preferably from 1 to 10 mole %, based on the organic compound to be silylated.

The silylation reaction proceeds smoothly without use of any catalyst when an acid having high acidity such as, for example, $CF_3SO_2$-OH is used. However, the reaction rarely proceeds in the absence of the catalyst when moderately or weakly acidic compounds such as acetic acid, alcohols, organic amines and the like are used. Thus, the use of catalyst depends on the type of starting organic compound having active hydrogen.

In order to carry out the process of the invention, an organic compound having active hydrogen and tert-butyldimethylsilane are mixed together and reacted at a temperature defined before in the presence or absence of a catalyst as set out before. The reaction time may vary depending upon the type of organic compound and the presence or absence of catalyst and the reaction temperature and is generally in the range of from 1 to 10 hours.

By the reaction, a t-butyldimethylsilylated product is obtained along with hydrogen generated as a side product. The product is separated and purified by any known techniques such as distillation or column chromatography. t-Butyldimethylsilane should preferably be used in amounts equimolar to or larger than that of compound to be silylated. However, too large an amount is not economical and it is general to use the silane in an amount of 1 to 3 times by mol, preferably 1.05 to 1.5 times by mol, that of compound to be silylated.

It will be noted that the reaction may be carried out in the absence of any solvent but a solvent may be used. Suitable solvents include, for example, hydrocarbons such as n-hexane, cyclohexane and the like, halogenated hydrocarbons such as dichloromethane, chloroform, dichloroethane and the like, ethers such as diethyl ether, dibutyl ether, tetrahydrofuran and the like, nitriles such as acetonitrile, and aromatic hydrocarbons such as benzene, toluene, xylene and the like. The reaction temperature and time may depend on the type of solvent, if used.

The present invention is more particularly described by way of examples.

EXAMPLE 1

Preparation of the t-butyldimethylsilyl derivative of 3-phenyl-1-propanol

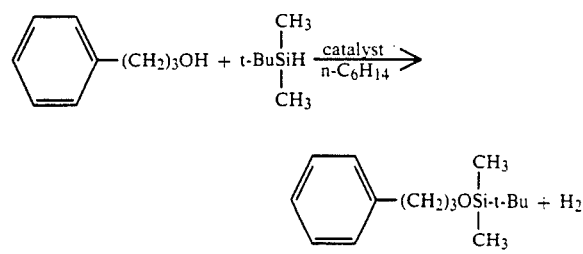

A small-size, two-necked flask was filled with an argon gas, into which 53.2 mg (0.05 mmols) of 10% Pd on carbon was placed. Thereafter, 136.2 mg (1.00 mmol) of 3-phenyl-1-propanol dissolved in 1.5 ml of dry n-hexane was charged into the flask, followed by further charge of 174.4 mg (1.5 mmols) of t-butyldimethylsilane and 2.0 ml of dry n-hexane. The solution was agitated at 25° C. After 2 hours, the resultant reaction product was sampled and subjected to gas chromatography, revealing that the conversion of the propanol into the silyl derivative was 96%. At this stage, the reaction was stopped. The Pd/C catalyst was removed by filtration, followed by removal of the solvent and unreacted t-butyldimethylsilane under reduced pressure.

As a result, a colorless, oily silylated product of the following formula was obtained at a yield of 89%.

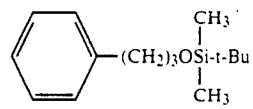

The product was subjected to NMR and IR spectrum analyses with the following results.

NMR analysis: $^1$H-NMR (CDCl$_3$, 90MHz), δ0.05 (s, 6H), 0.1 (s, 9H), 1.7–2.0(m, 2H), 3.63(t, 2H), 7.2–7.3(m, 5H)

IR analysis: IR (neat) cm$^{-1}$ 1490, 1460, 1385, 1250, 1100, 960, 830, 770, 735, 690

EXAMPLE 2-8

The general procedure of Example 1 was repeated except that the type of catalyst, reaction temperature and reaction time were changed, thereby obtaining the following results

| Example | Catalyst (5 mol %) | Temperature (°C.) | Time (hrs.) | Conversion (%) |
| --- | --- | --- | --- | --- |
| 2 | (RhCN)$_2$PdCl$_2$ | 60 | 5 | 48 |
| 3 | PdCl$_2$ | 55 | 5 | 25 |
| 4 | 10% Pd/C | 25 | 2 | 96 |
| 5 | 10% Pd/C | 70 | 2 | 100 |
| 6 | 10% Rh/C | 70 | 1 | 99 |
| 7 | 10% Ru/C | 70 | 4 | 96 |
| 8 | nil | 70 | 10 | 0 |

EXAMPLES 9–13

Preparation of the t-butyldimethylsilyl derivative of cyclohexanol

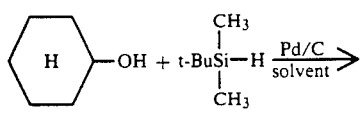

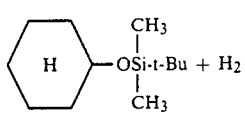

The general procedure of Example 1 was repeated except that cyclohexanol was used as the starting compound and the reaction temperature and time were changed along with the type of solvent indicated below. The product obtained by the respective procedures was isolated by gas chromatography and subjected to NMR and IR analyses. The results of the analyses and the conversion are summarized below.

NMR analysis: $^1$H-NMR (CDCl$_3$, 90MHz), $\delta$0.05 (s, 6H), 0.89(s, 9H), 1.1–1.9(m, 10H), 3.4–3.8 (m, 1H)

IR analysis: IR (neat) cm$^{-1}$ 1470, 1460, 1445, 1370, 1360, 1250, 1135, 1095, 1050, 1015, 1005, 995, 885, 870, 835, 770, 660

| Example | Solvent | Temperature (°C.) | Time (hrs.) | Conversion (%) |
|---|---|---|---|---|
| 9 | n-C$_6$H$_{14}$ | 70 | 7 | 92 |
| 10 | CH$_2$Cl$_2$ | 40 | 5 | 22 |
| 11 | THF | 70 | 19 | 19 |
| 12 | CH$_3$CN | 40 | 5 | 11 |
| 13 | C$_6$H$_6$ | 70 | 19 | 9 |

EXAMPLE 14

Preparation of the t-butyldimethylsilyl derivative of morpholine

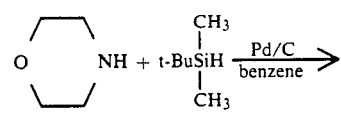

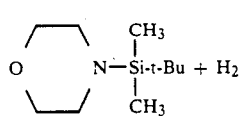

The general procedure of Example 1 was repeated exept that morpholine was used as the starting material and benzene was used as the solvent. The conversion into the derivative was 93%.

The formation of the silyl derivative was confirmed through NMR analysis.

NMR analysis: $^1$-NMR (CDCl$_3$, 90MHz), $\delta$0.03 (s, 6H), 0.86(s, 9H), 2.8–3.0(m, 4H), 3.4–3.6 (m, 4H)

EXAMPLES 15–18

The general procedure of Example 14 was repeated except that the solvent, reaction temperature and time were changed, with the following results.

| Example | Solvent | Temperature (°C.) | Time (hrs.) | Conversion (%) |
|---|---|---|---|---|
| 15 | n-C$_6$H$_{14}$ | 70 | 4 | 59 |
| 16 | CH$_2$Cl$_2$ | 40 | 4 | 41 |
| 17 | THF | 70 | 4 | 70 |
| 18 | CH$_3$CN | 80 | 4 | 84 |

EXAMPLE 19

Preparation of the t-butyldimethylsilyl derivative of 3-phenylpropionic acid:

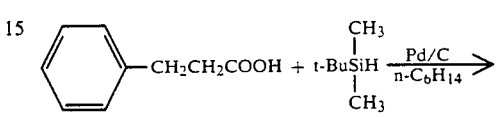

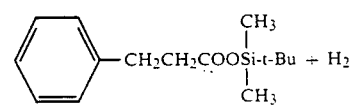

The general procedure of Example 1 was repeated except that phenylpropionic acid was used and the reaction temperature and time were changed as indicated below. The results are shown below.

| Temperature (°C.) | Time (hours) | Conversion (%) |
|---|---|---|
| 50 | 5 | 89 |

The formation of the silyl derivative was confirmed through NMR and IR analyses.

NMR analysis: $^1$H-NMR (CDCl$_3$, 90MHz), $\delta$0.26 (s, 6H), 0.93(s, 9H), 2.5–2.8 (m, 2H), 2.8–3.1 (m, 2H), 7.25 (s, 5H)

IR analysis: IR (neat) cm$^{-1}$ 1720, 1605, 1495, 1460, 1410, 1365, 1290, 1255, 1190, 1075, 945, 870, 840, 820, 805, 790, 740, 695

EXAMPLE 20

Preparation of the t-butyldimethylsilyl derivative of 4-hydroxymethyl-2-azetidinone

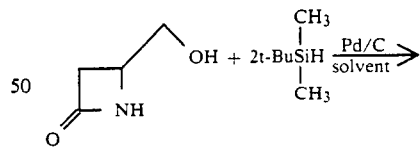

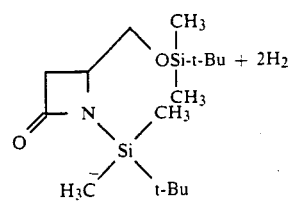

All of the reaction systems used an atmosphere of argon. A two-necked flask was provided, into which 10.6 mg (0.01 mmol) of 10% Pd on carbon (10% Pd/C) and 33.8 g (0.33 mmols) of 4-hydroxymethyl-2-azetidinone were charged. Thereafter, 116.24 mg (1.00 mmol) of t-butyldimethylsilane dissolved in 1.5 ml of dry n-C$_6$H$_{14}$ was added to the mixture. In this state, dissolution was not complete, and 1.5 ml of dry $CH_2Cl_2$ was further added to the mixture. The resultant solution was agitated at 25° C. for 2 hours, after which the Pd/C catalyst was removed by filtration. The solvent and excess t-butyldimethylsilane were distilled off from the filtrate to obtain an N,O-di-silylated product of the 4-hydroxymethyl-2-azetidinone was obtained as a colorless transparent oily substance. The yield was 80%. The product was confirmed through NMR.

NMR analysis: $^1H$-NMR ($CDCl_3$, 90MHz), δ0.06 (s, 6H), 0.22 (s, 3H), 0.24 (s, 3H), 0.90 (s, 9H), 0.96(s, 9H), 2.5–3.2 (m, 2H), 3.4–3.8 (m, 3H)

What is claimed is:

1. A silylation process which comprises reacting tert-butyldimethylsilane of the formula, $(CH_3)_3CSiH(CH_3)_2$, and an organic compound containing an active hydrogen reactive with the t-butyldimethylsilane, the reaction being carried out at a temperature of from 20° C. to 200° C., optionally in the presence of a dehydrogenative silylation catalyst.

2. The process according to claim 1, wherein said organic compound is an alcohol of the formula, R-OH, wherein R represents an unsubstituted or substituted linear or branched alkyl group, aryl group or aralkyl group.

3. The process according to claim 1, wherein said organic compound is a primary amine of the formula, $R^1$-$NH_2$, wherein $R^1$ represents an unsubstituted or substituted, linear or branched alkyl group, aryl group or aralkyl group.

4. The process according to claim 1, wherein said organic compound is a secondary amine of the formula, $$R^1-NH\overset{R^2}{|}$$

wherein $R^1$ and $R^2$ independently represent an unsubstituted or substituted, linear or branched alkyl group, aryl group or aralkyl group.

5. The process according to claim 1, wherein said organic compound is a carboxylic acid of the formula, $R^3$-COOH, wherein $R^3$ represents an unsubstituted or substituted, linear or branched alkyl group, aryl group or aralkyl group.

6. The process according to claim 1, wherein said organic compound is 4-hydroxymethyl-2-azetidinone.

7. The process according to claim 1, wherein said catalyst is a metal of Group VIII of the periodic table or its compound.

8. The process according to claim 7, wherein said metal is Ru, Rh or Pd.

9. The process according to claim 8, wherein said metal is supported on carbon.

10. The process according to claim 7, wherein said catalyst is a compound selected from the group consisting of $PdCl_2$, $[Pd(\pi^3-C_3H_5)Cl]_2$ and $$(NC-\!\!\!\bigcirc\!\!\!-)_2PdCl_2.$$

11. The process according to claim 1, wherein the reaction is carried out in a solvent.

12. The process according to claim 1, wherein the reaction is carried out under heating conditions at a temperature ranging from 40° to 150° C.

13. A silylation process which comprises reacting a strongly acidic compound and t-butyldimethylsilane at a temperature of from 20° C. to 200° C.

14. The process according to claim 13, wherein the reaction is carried out in a solvent.

15. The process according to claim 13, wherein said strongly acidic compound is $CF_3SO_2$-OH.

16. A silylation process to protect active hydrogen substituents contained on an organic compound and produce a non-iron corrosive product wherein the active hydrogen on said organic compound is resistant at the protective group to the Grignard reaction, the Wittig reaction, diisobutyl aluminum hydride reduction, and the Jones oxidation, but wherein the protective group can be readily removed by the action of F ions, the process comprising the reaction of tertiarybutyldimethysilane of the formula $(CH_3)_3CSiH(CH_3)_2$, with said organic compound containing said active hydrogen site, the reaction being carried out in the presence of a solvent, at a temperature from 40° to 150° C. and in the presence of a catalyst to effect a dehydrogenative silylation reaction.

17. A process according to claim 16 wherein the silylated product resulting from the reaction is separated and purified by distillation or column chromatography.

18. A process according to claim 16 wherein one to three moles of the silane is reacted per mole of the organic compound.

* * * * *